(12) United States Patent
Heyd et al.

(10) Patent No.: US 10,092,435 B2
(45) Date of Patent: Oct. 9, 2018

(54) ANKLE BRACE AND METHOD OF MAKING THE SAME

(75) Inventors: Davin T. Heyd, Delavan, WI (US);
William D. Falcon, Elkhorn, WI (US);
Timothy F. O'Keefe, Delavan, WI (US)

(73) Assignee: Bracemasters International, LLC, Delavan, WI (US)

( * ) Notice: Subject to any disclaimer, the term of this patent is extended or adjusted under 35 U.S.C. 154(b) by 23 days.

(21) Appl. No.: 14/354,482

(22) PCT Filed: Oct. 28, 2011

(86) PCT No.: PCT/US2011/058317
§ 371 (c)(1),
(2), (4) Date: Apr. 25, 2014

(87) PCT Pub. No.: WO2013/062579
PCT Pub. Date: May 2, 2013

(65) Prior Publication Data
US 2014/0309572 A1    Oct. 16, 2014

(51) Int. Cl.
*A61F 5/00* (2006.01)
*A61F 5/01* (2006.01)

(52) U.S. Cl.
CPC .......... *A61F 5/0102* (2013.01); *A61F 5/0111* (2013.01)

(58) Field of Classification Search
CPC ........ A61F 5/0102; A61F 5/0111; A61F 5/01; A61F 5/0195; A61F 5/04; A61F 5/05; A61F 13/066; A61F 5/0127; A61F 13/065
USPC ............... 602/5, 6, 23, 27, 65, 66; 128/882; D24/192; D2/913
See application file for complete search history.

(56) References Cited

U.S. PATENT DOCUMENTS

| | | | |
|---|---|---|---|
| 1,037,441 A | 9/1912 | Collis | |
| 1,930,188 A * | 10/1933 | Arthur | A61F 13/064 602/66 |
| 2,994,322 A | 8/1961 | Cullen et al. | |
| 3,333,353 A | 8/1967 | Garcia | |
| 3,970,083 A | 7/1976 | Carrigan | |
| 4,187,844 A * | 2/1980 | Caprio, Jr. | A61F 5/0111 602/65 |
| D255,384 S | 6/1980 | Finnieston | |
| 4,280,488 A | 7/1981 | Polsky et al. | |
| 4,489,719 A * | 12/1984 | Lapenskie | A43B 7/20 36/89 |
| 4,863,779 A * | 9/1989 | Daponte | B32B 7/14 428/152 |
| 4,878,505 A | 11/1989 | Thanner | |

(Continued)

FOREIGN PATENT DOCUMENTS

WO    2011/113473 A1    9/2011

OTHER PUBLICATIONS

AS1 Ankle Brace-Active Ankle; www.activeankle.com; at least as early as Dec. 2012; 2 pages.
(Continued)

*Primary Examiner* — Ophelia A Hawthorne
*Assistant Examiner* — Caitlin Carreiro
(74) *Attorney, Agent, or Firm* — Husch Blackwell LLP (57) ABSTRACT

An ankle brace having a brace body, first reinforcement strips, second reinforcement strips, and a closure mechanism provides medial-lateral support. The ankle brace may be custom or pre-fabricated.

18 Claims, 7 Drawing Sheets

(56) References Cited

U.S. PATENT DOCUMENTS

| | | | |
|---|---|---|---|
| 4,998,537 A | 3/1991 | Rau | |
| D339,671 S | 9/1993 | Manning | |
| 5,370,604 A | 12/1994 | Bernardoni | |
| 5,456,976 A | 10/1995 | LaMarca, II et al. | |
| 5,472,414 A | 12/1995 | Detty | |
| 5,501,659 A | 3/1996 | Morris et al. | |
| 5,657,767 A | 8/1997 | Nelson et al. | |
| 5,713,837 A | 2/1998 | Grim et al. | |
| D394,112 S | 5/1998 | Duback et al. | |
| 5,814,002 A | 9/1998 | Nelson | |
| 5,853,380 A | 12/1998 | Miller | |
| 6,024,712 A | 2/2000 | Iglesias et al. | |
| 6,083,184 A | 7/2000 | Kenosh | |
| 6,155,997 A | 12/2000 | Castro | |
| D440,661 S | 4/2001 | Cionitti | |
| 6,212,743 B1 | 4/2001 | Cohen | |
| 6,394,917 B1 | 5/2002 | Chiappini et al. | |
| 6,517,505 B1 | 2/2003 | Veldman | |
| 6,540,705 B2 | 4/2003 | Norstrem et al. | |
| 6,652,474 B1 | 11/2003 | Quinn et al. | |
| 6,663,584 B2 | 12/2003 | Griesbach, III et al. | |
| 6,767,332 B1 * | 7/2004 | Pardue | A61F 5/0111 128/882 |
| D509,586 S | 9/2005 | Lee | |
| 7,014,621 B2 | 3/2006 | Nelson | |
| 7,018,351 B1 * | 3/2006 | Iglesias | A61F 5/0111 128/882 |
| D548,846 S | 8/2007 | Buethorn | |
| D552,744 S | 10/2007 | Verkade et al. | |
| D559,988 S | 1/2008 | Buethorn | |
| 7,513,881 B1 | 4/2009 | Grim et al. | |
| 7,651,472 B2 | 1/2010 | Gaylord et al. | |
| 7,691,076 B2 | 4/2010 | Castro | |
| 7,867,180 B2 | 1/2011 | Cuypers et al. | |
| 7,918,811 B2 | 4/2011 | Lussier et al. | |
| 7,950,676 B2 | 5/2011 | Goldsmith et al. | |
| D639,965 S | 6/2011 | Wehsely-Swiczinsky | |
| 7,993,295 B2 | 8/2011 | Nelson | |
| D649,650 S | 11/2011 | Wehsely-Swiczinsky | |
| D682,434 S | 5/2013 | Heyd et al. | |
| 8,512,269 B1 | 8/2013 | Stano et al. | |
| D696,409 S | 12/2013 | Best et al. | |
| D708,344 S | 7/2014 | Best et al. | |
| D722,382 S | 2/2015 | Lee et al. | |
| 2003/0083603 A1 * | 5/2003 | Nelson | A61F 5/0111 602/27 |
| 2004/0034316 A1 | 2/2004 | Castro | |
| 2005/0096576 A1 * | 5/2005 | Castro | A61F 5/0127 602/27 |
| 2009/0076428 A1 | 3/2009 | Kay | |
| 2010/0094392 A1 | 4/2010 | Nguyen et al. | |
| 2011/0196276 A1 | 8/2011 | Kuhn | |
| 2014/0188026 A1 | 7/2014 | Gaylord | |
| 2014/0213953 A1 | 7/2014 | Heyd et al. | |
| 2014/0243724 A1 | 8/2014 | Dodin | |
| 2014/0276314 A1 | 9/2014 | Heyd et al. | |

OTHER PUBLICATIONS

CF Pro Ankle Brace-Active Innovations; www.activeankle.com; at least as early as Dec. 2012; 2 pages.
DRAFO Caregiver Guide; Bracemasters International, LLC; www.bracemasters.com; Apr. 2011; 2 pages.
DRAFO Clinical Education Workshop; Bracemasters International, LLC; www.bracemasters.com; Apr. 2011; 2 pages.
DRAFO DRG; Bracemasters International, LLC; www.bracemasters.com; Apr. 2010; 2 pages.
DRAFO Introduction; Bracemasters International, LLC; www.bracemasters.com; Apr. 2011; 2 pages.
DRAFO Practitioner Toolbox; Bracemasters International, LLC; www.bracemasters.com; Apr. 2011; 2 pages.
DRAFO Selection Guide; Bracemasters International, LLC; www.bracemasters.com; Apr. 2011; 2 pages.
DRAFO Sport—The Ultimate Solution for Athletic Ankle Bracing; Bracemasters International, LLC; www.bracemasters.com; May 2011; 2 pages.
DRAFO Sport advertisement; Bracemasters International, LLC; www.bracemasters.com; May 2011; 1 page.
Excel Ankle Brace—Active Ankle; www.activeankle.com; at least as early as Dec. 2012; 2 pages.
EZ Lacer Ankle Brace-Active Ankle; www.activeankle.com; at least as early as Dec. 2012; 2 pages.
Gehlsen, G. et al.; Ankle Joint Strength, Total Work, and ROM; Comparison Between Prophylactic Devices; Athletic Training JNATA; vol. 26, Spring 1991; available at www.activeankle.com; 4 pages.
Gehlsen, G. et al.; Subtalar Joint Movement During Running on Camber: Comparison Between Prophylactic Devices; Ball State University; at least as early as Dec. 2012; available at www.activeankle.com; 1 page.
Johnson, R. et al.; Comparative Study of Ankle Support Devices; Journal of the Emerican Podiatric Medical Association; vol. 84, No. 3; Mar. 1994; available at www.activeankle.co; 1 page.
Multi-Phase Ankle Brace-Active Innovations; www.activeankle.com; at least as early as Dec. 2012; 2 pages.
Need value? Quality? Results? Think DRAFO; Bracemasters International, LLC; www.bracemaster.com; Sep. 2010; 3 pages.
Notification of Transmittal of International Search Report and Written Opinion of the International Searching Authority; International Application No. PCT/US2011/058317; dated Feb. 13, 2012; 7 pages.
Ossur Form Fit® Ankle Brace; http://www.ossurcom/?PageID=13539; at least as early as Dec. 2012; 2 pages.
Parekh, S. et al.; Prophylactic Bracing Decreases Ankle Injuries in Collegiate Female Volleyball Players; University of North Carolina; University of Pennsylvania; at least as early as Dec. 2012; available at www.activeankle.com; 2 pages.
Power Lacer Ankle Brace-Active Ankle; www.activeankle.com; at least as early as Dec. 2012; 2 pages.
Pro Med Ankle Brace-Active Innovations; www.activeankle.com; at least as early as Dec. 2012; 2 pages.
Richie Brace—Custom Articulated Ankle Foot Orthosis; www.footcareexpress.com/services/richie_brace_php; Copyright © 2011; 5 pages.
Siegler, S. et al.; Heel Pain Control Characteristics of the Active Ankle Brace; Drexel University; at least as early as Dec. 2012; available at www.activeankle.com; 1 page.
Siegler, S. et al.; The Three Dimensional Passive Support Characteristics of Ankle Braces; presented at the 1996 American College of Foot and Ankle Surgeons Meeting and Scientific Seminar; available at www.activeankle.com; 2 pages.
T1 Ankle Brace-Active Ankle; www.activeankle.com; at least as early as Dec. 2012; 2 pages.
T2 Ankle Brace-Active Ankle; www.activeankle.com; at least as early as Dec. 2012; 2 pages.
The DRAFO Difference; Bracemasters International, LLC; www.bracemasters.com; Sep. 2011; 2 pages.
The DRAFO DRG—Dynamic Response Gauntlet—Practitioner's Guide; Bracemasters International, LLC; www.bracemasters.com; published after Oct. 28, 2011; 2 pages.
The Richie Brace; Precision Orthotic Lab International; www.precisionorthotic.com/precision/products/richiebrace.htm; Copyright © 2004; 3 pages.
Volt Ankle Brace-Active Ankle; www.activeankle.com; at least as early as Dec. 2012; 2 pages.

* cited by examiner

ANKLE BRACE AND METHOD OF MAKING THE SAME

BACKGROUND

1. Field of the Invention

This invention relates to providing a custom or prefabricated ankle brace. The ankle brace provides medial-lateral support yielding varus and valgus control to protect from excessive rotation or extreme medial-lateral motion that could go beyond normal end-range of motion, causing injury. This invention protects against ankle instability or injury during normal or extreme human locomotion.

2. Description of the Related Art

Typical ankle support orthoses use flexible materials to provide a comfortable fit and little, if any, motion restriction, and thus are very limited in support. These ankle braces may not prevent injury in excessive activity associated with physical exercise programs or athletic events. Ankle braces which do include a combination of fabric cover with rigid or semi-rigid inserts, provide support but severely limit ankle mobility. In addition, current ankle braces suffer from lack of durability, especially if the person using them is involved in aggressive athletic activity.

In response to the limitations of such ankle braces, the athletic industry typically uses adhesive tape to protect athletes since it provides an adequate support, but often limits mobility. However, adhesive tape is not durable and often breaks down during use. The tape is generally not re-usable. Still further, before every athletic event a person needs to take the time to tape their ankle.

There exists a need in improving conventional ankle braces to treat acute or chronic ankle conditions without either limiting mobility or failing to provide sufficient support, while offering a level of comfort and durability suitable for intense, athletic applications that can be worn inside a common civilian or athletic footwear. The improved ankle brace would be durable, reusable and provide the correct balance between support and mobility when used in conjunction with a shoe.

SUMMARY

The present disclosure provides an ankle brace comprising a combination of a thermoforming plastic material for the brace body and a different material for the reinforcement strips. Not only does the present disclosure provide a combination of specific materials varied in stiffness, but it provides a specific relative amount and placement of the reinforcement strip material in relation to the thermoforming plastic to yield an ankle brace having an improved combination of support and flexibility to prevent injury.

In one embodiment the disclosure provides an ankle brace arranged to provide varus and valgus control and medial-lateral inversion or eversion control comprising a brace body comprising a medial side portion, a lateral side portion, a medial front edge of the medial side portion, a lateral front edge of the lateral side portion, a sole portion in a plane at least partially horizontal to the medial and lateral side portions having an arch portion and a heel portion, and a back portion extending from the heel portion to a lower calf portion. The brace body comprises a polyolefin elastomeric material. The ankle brace comprises a first medial reinforcement strip extending down and along the medial side portion, a first lateral reinforcement strip extending down and along the lateral side portion, a second medial reinforcement strip having one end intersecting with the first medial reinforcement strip, wherein the second medial reinforcement strip extends substantially parallel to the medial front edge of the medial side portion, a second lateral reinforcement strip having one end intersecting with the first lateral reinforcement strip, wherein the second lateral reinforcement strip extends substantially parallel to the lateral front edge of the lateral side portion, and at least one closure mechanism in contact with at least one reinforcement strip wherein the closure mechanism tightens and secures the ankle brace.

The present disclosure also provides a method of manufacturing an ankle brace comprising the steps of providing a mold of a lower extremity, placing at least one reinforcement strip on the mold for varus and valgus control, forming a polyolefin elastomeric material over the mold, reinforcement strips and base of the lace loops to produce a brace body wherein the reinforcement strips and base of lace loops are inset into the polyolefin elastomeric material, and removing the mold to produce the ankle brace.

BRIEF DESCRIPTION OF THE DRAWINGS

The disclosure is described generally with reference to the drawings for the purpose of illustrating certain embodiments only, and not for the purpose of limiting the scope of the invention. In the drawings like numerals are used to designate like parts throughout the same.

DETAILED DESCRIPTION

Ankle Brace

Figure 1A:
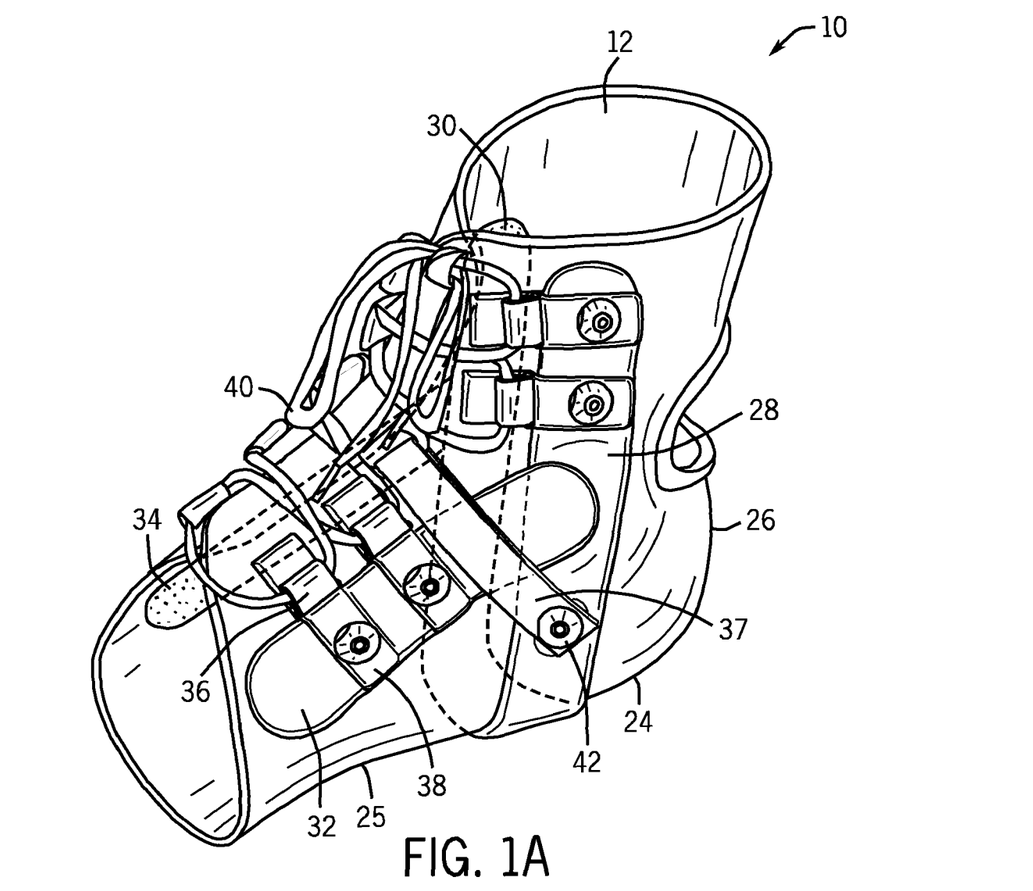
FIG. 1A is a perspective view of an embodiment of the ankle brace.

The present disclosure provides an ankle brace assembly arranged to provide varus and valgus control and stabilize the talus (subtalar and mid-tarsal joints). As depicted in FIG. 1A, ankle brace 10 comprises brace body 12, first reinforcement strips, second reinforcement strips, lace loops, and a closure mechanism to tighten and secure the ankle brace.

An advantage of the ankle brace assembly disclosed herein is the placement of the reinforcement strips in relation to the thermoforming plastic of the brace body to yield an ankle brace having an improved combination of support and flexibility to prevent injury. Specifically, as shown in FIG. 1B, ankle brace 10 allows for dorsiflexion and plantarflexion motion about the x-axis, while maintaining the support necessary to hinder medial-lateral rotation about the y-axis.

Figure 2A:
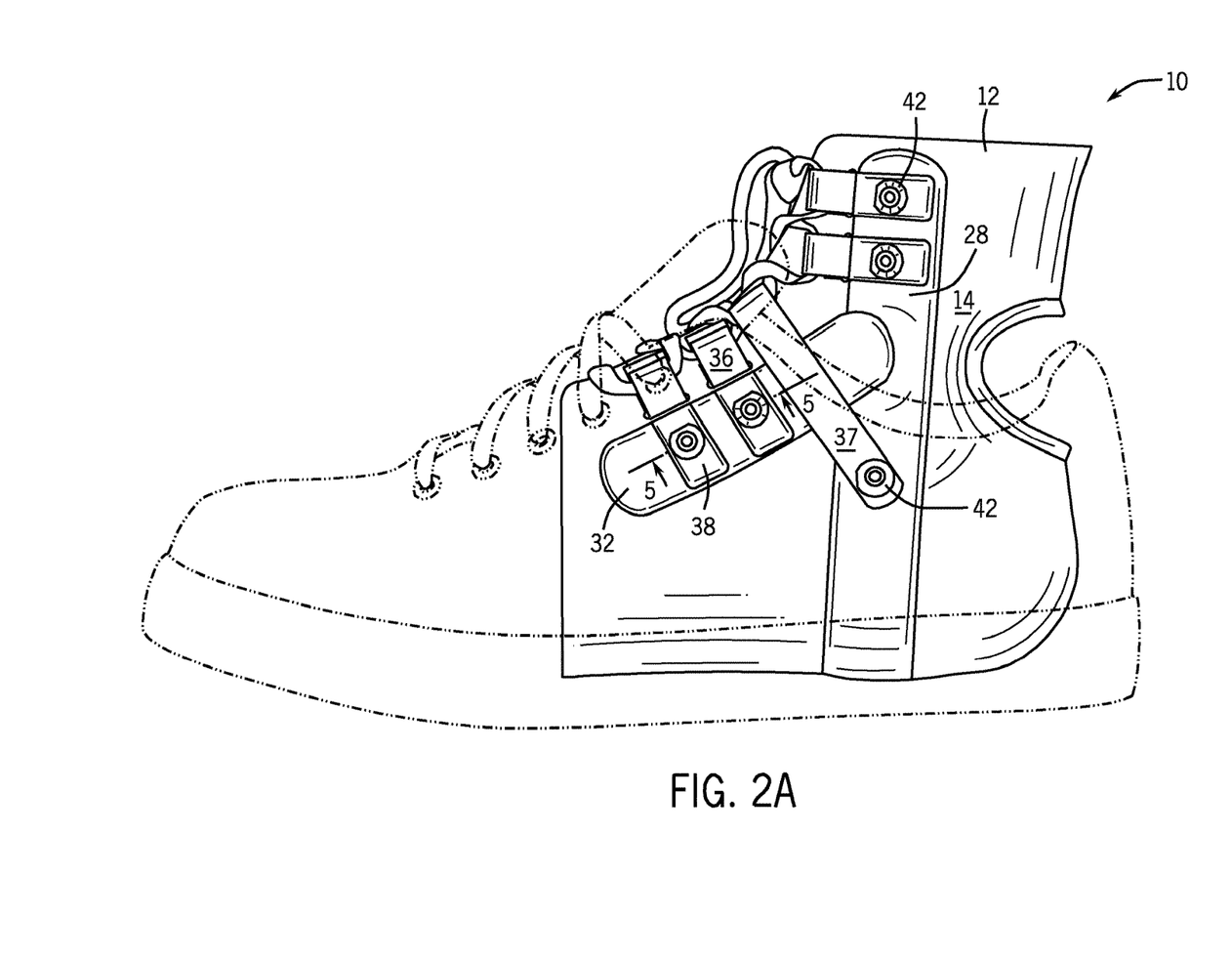
FIG. 2A is medial side view of an embodiment of the ankle brace inside a shoe.
Figure 2B:
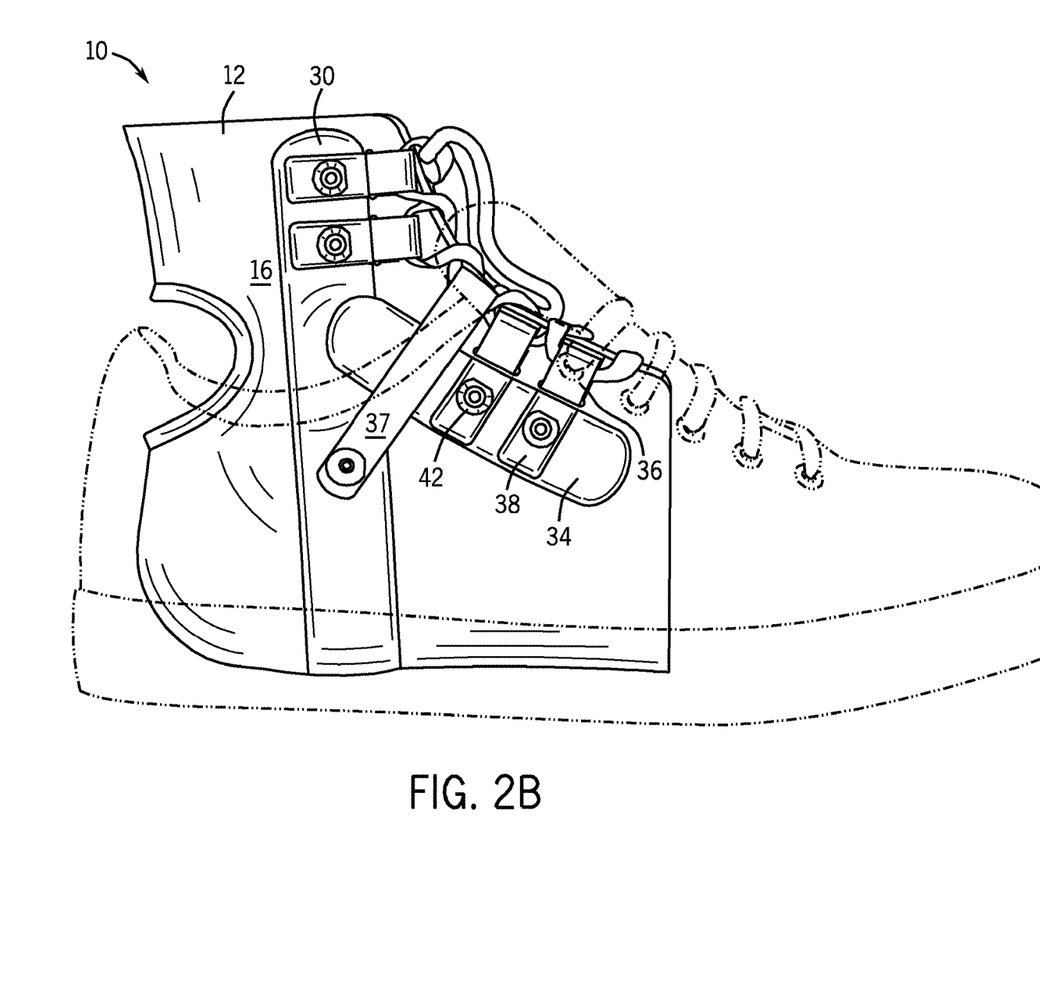
FIG. 2B is lateral side view of an embodiment of the ankle brace inside a shoe.

FIGS. 2A and 2B are medial and lateral side views, respectively, of an embodiment of ankle brace 10 used in combination with a normal shoe. The ankle brace is designed to be worn over socks and inside most standard shoes without the need to increase the shoe size to accommodate for the ankle brace.

Figure 1B:
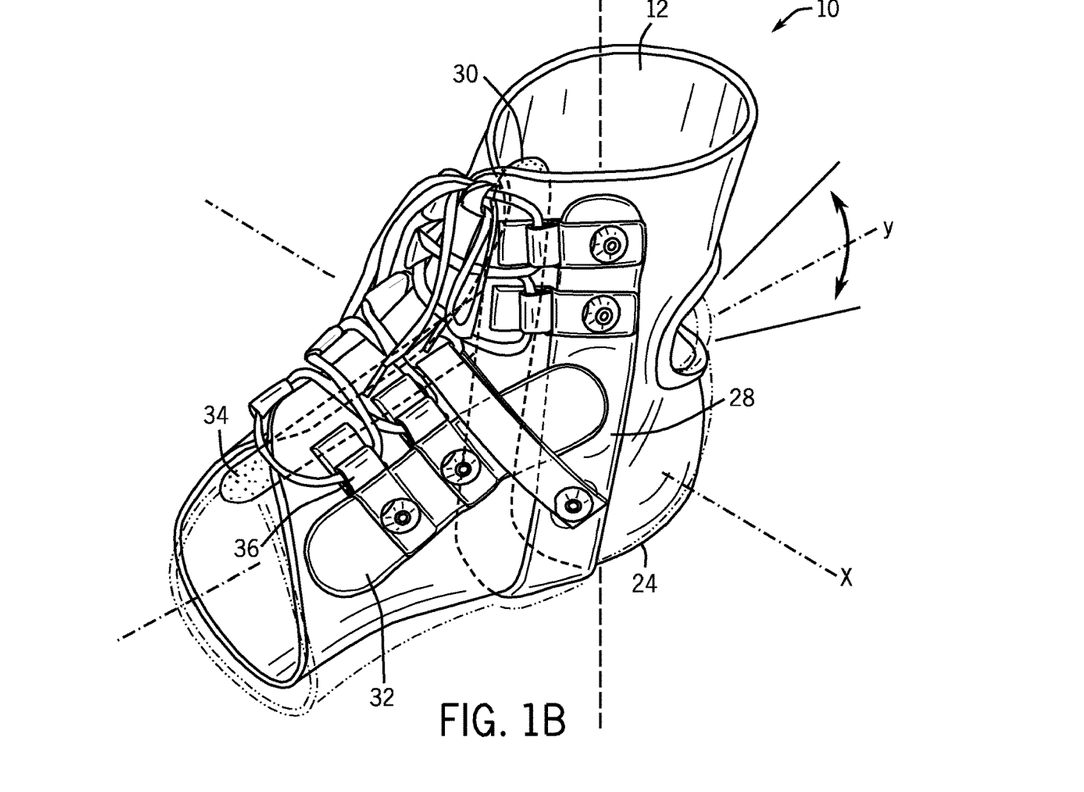
FIG. 1B is a perspective view of an embodiment of the ankle brace.
Figure 3:
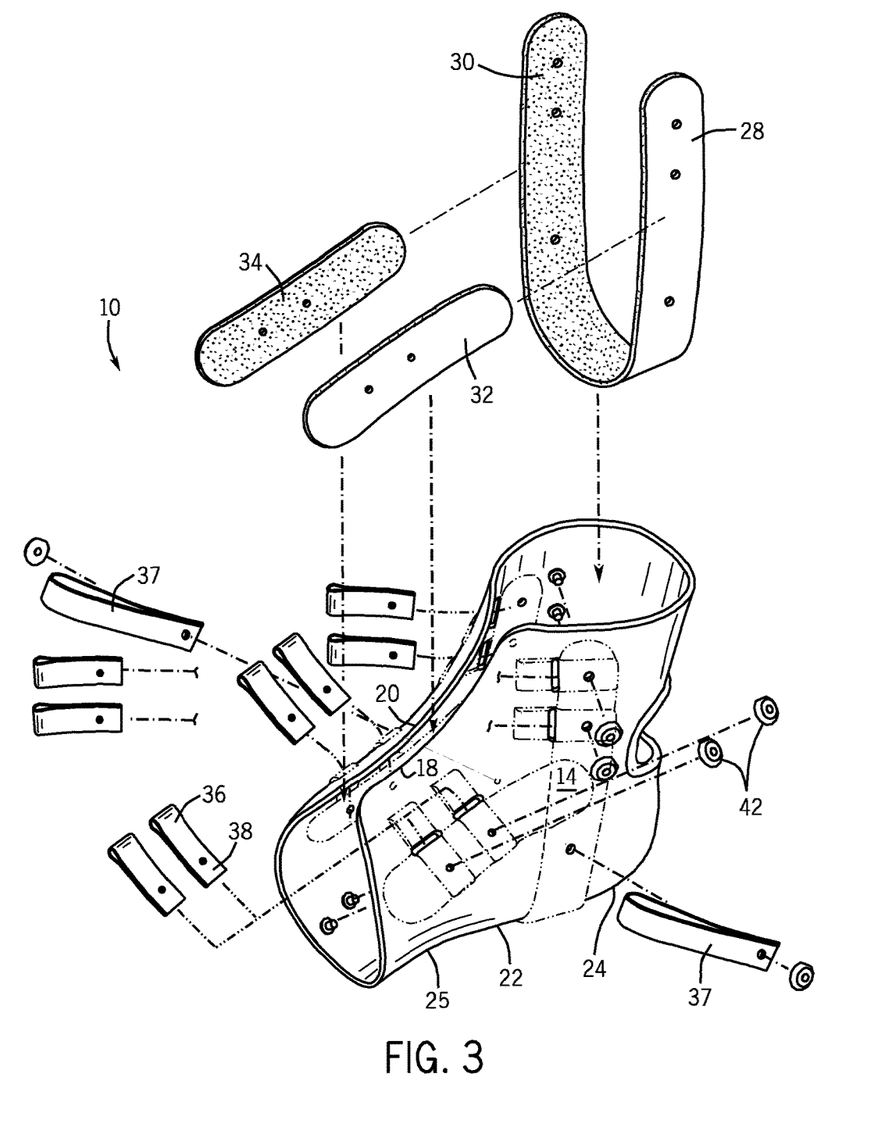
FIG. 3 is an exploded view FIG. 1.

As shown in FIGS. 1-3, brace body 12 is typically toe-less and in the general shape of a boot. Brace body 12 comprises medial side portion 14, lateral side portion 16, medial front edge 18 of medial side portion 14, lateral front edge 20 of lateral side portion 16, sole portion 22, heel portion 24 and back portion 26. Sole portion 22 is at least partially in a horizontal plane perpendicular to medial side portion 14 and lateral side portion 16. Sole portion 22 has arch portion 25 and heel portion 24. Back portion 26 extends, as shown, upwardly and substantially vertically, from heel portion 24 to lower calf portion 27.

In an embodiment, the brace body is made of a polyolefin elastomeric material having thermoforming capabilities. Preferably the polyolefin elastomeric material is an ethylene-butene copolymer or an ethylene-octene copolymer having a melt index range at 190° C. of less than 0.5 to 30 g/10 min (measured according to ASTM D 1238), a density of 0.857 to 0.910 g/cm$^3$ (measured according to ASTM D 792), a melting range of 36° C. to 104° C., a Shore A Hardness of 56 to 96 (ASTM D 2240), and a flexural modulus from 3 to 110 MPa (measured according to ASTM D 790).

In an embodiment, the polyolefin elastomeric material is an ethylene-butene copolymer having a density of 0.885 g/cm$^3$ (measured according to ASTM D 792), a melt index of 2 g/10 min (2.16 kg @ 190° C. measured by ASTM D 1238), a Mooney Viscosity of 13 (ML 1+4 @121° C., measured according to ASTM 1646), a Shore A durometer hardness of 82 (measured according to ASTM 2240) and an ultimate tensile strength of 11.2 MPa (508 mm/min measured according to ASTM D 638).

An advantage of the polyolefin elastomeric material used in the brace body is that the ankle brace is essentially waterproof. Therefore, a user may use the ankle brace in hydrotherapy or other water immersed activities.

Figure 4:
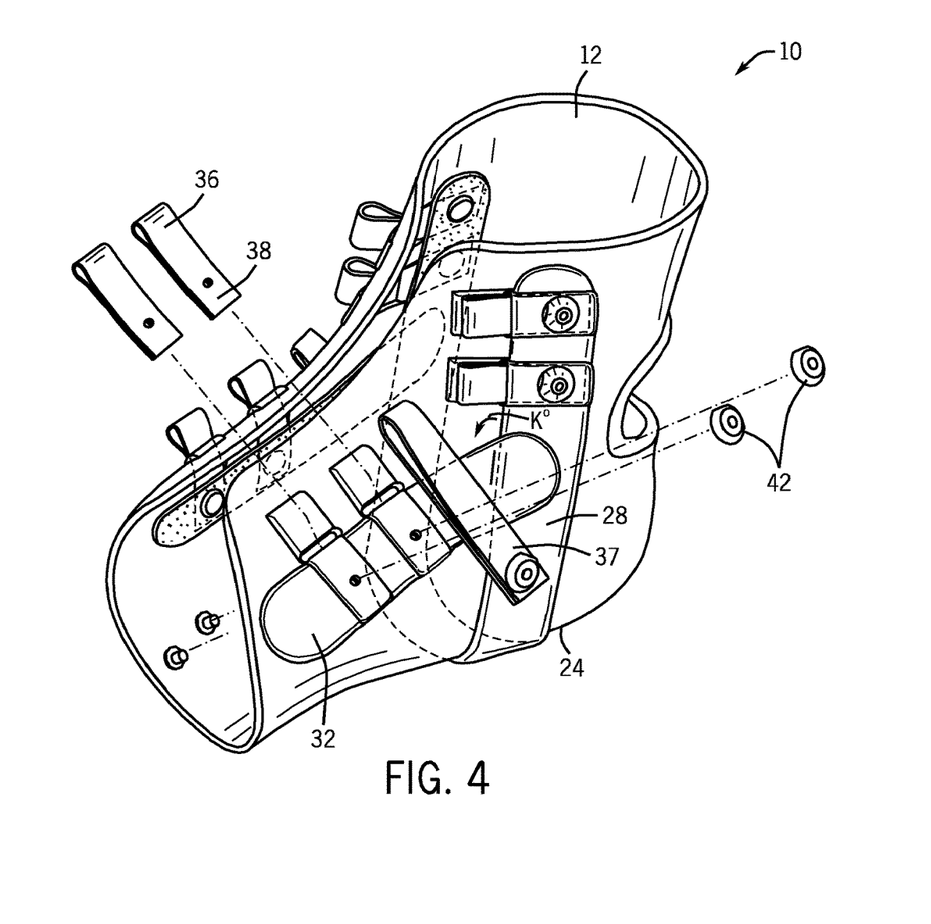
FIG. 4 is a partially assembled view of FIG. 3.

As shown in the exploded view in FIG. 3 and FIG. 4, the ankle brace further comprises first reinforcement strips: first medial reinforcement strip 28 and first lateral reinforcement strip 30. First medial reinforcement strip 28 extends down and along medial side portion 14 of brace body 12 and first lateral reinforcement strip 30 extends down and along lateral side portion 20 of brace body 12. In an embodiment, the first medial reinforcement strip portion and the first lateral reinforcement strip portion are one continuous reinforcement strip that extends around heel portion 24 of brace body 12. In an embodiment, the first reinforcement strips hinder motion in the z-x plane about the y-axis in FIG. 1b. In an embodiment, the first reinforcement strips are from 0.5 to 1.5 inches in width, for example from 0.9 to 1.2 inches. In an embodiment, the first reinforcement strips are from 3 to 12 inches in length, for example from 7 to 10 inches, for example 8.5 to 9.5 inches.

Ankle brace 10 further comprises second reinforcement strips: second medial reinforcement strip 32 and second lateral reinforcement strip 34. Second medial reinforcement strip portion 32 extends from first medial reinforcement strip 28, wherein second medial reinforcement strip 32 extends substantially parallel to medial front edge 18 of medial side portion 14 of brace body 12. In an embodiment, one end of second medial reinforcement strip portion 32 intersects, so as to overlay, with first medial reinforcement strip 28. In an embodiment, as shown in FIG. 4, angle K° between second medial reinforcement strip 32 and first medial reinforcement strip 28 is from 90° to 120°, for example 100° to 110°.

Second lateral reinforcement strip portion 34 extends from first lateral reinforcement strip 30, wherein second lateral reinforcement strip 34 extends substantially parallel to lateral front edge 20 of lateral side portion 16 of brace body 12. In an embodiment, one end of second lateral reinforcement strip 32 intersects with first lateral reinforcement strip 28. In an embodiment, as shown in FIG. 4, angle K° between second lateral reinforcement strip portion 34 and first lateral reinforcement strip portion 30 is from 90° to 120°, for example 100° to 110°. In an embodiment, the second reinforcement strips are from 0.5 to 1.5 inches in width, for example from 0.9 to 1.2 inches. In an embodiment, the second reinforcement strips are from 2.5 to 6 inches in length, for example 4 to 5 inches.

Reinforcement strips are laminated or inset into the brace body to provide support in target areas without reducing the flexibility of the brace body in other areas. Target areas refer to areas coinciding with the reinforcement strips. The first medial and lateral reinforcement strips limit the range of medial-lateral motion in target areas to guard against excessive range of motion that could cause injury. When the ankle brace is properly fastened, the first reinforcement strips work in conjunction with the second reinforcement strips to control rotation and prevent excessive movement that will lead to injury.

As shown in FIG. 1B, the specific combination of reinforcement strips in the present disclosure limits ankle inversion and eversion in the z-x plane and prevents ankle rotation about the y-axis and z-axis. While preventing ankle inversion and eversion, the specific combination of reinforcement strips in the present disclosure allows for dorsiflexion and plantarflexion motion.

In an embodiment, the reinforcement strips are made of a durable fabric. In an embodiment, the reinforcement strips are made from the loop pile of a Velcro strip, available from Velcro USA, Inc. Alternatively, the reinforcement strips are made from a Scotch Mate Strip, available from 3M. In an embodiment, the reinforcement strips are made of a stiffer material than that of the polyolefin elastomeric material used in the brace body.

Ankle brace 10 comprises a closure mechanism 40 to tighten and secure the ankle brace. Closure mechanism 40 may include laces with lace loops, laces with lace hooks, Velcro, elastic closures, cinched straps, zippers, snaps, buttons, hooks, clasps, and fasteners. In an embodiment, when the closure mechanism is engaged, the lateral front edge and medial front edge of the brace body overlap such that the brace body does not require additional manufacturing of a tongue element to the ankle brace. The overlap may be from 0.125 inches to 1.5 inches, for example 0.25 inch to 1.0 inch.

In an embodiment, shown in FIG. 1A, ankle brace 10 includes a closure mechanism of lace loops and laces. For example, ankle brace 10 may further comprise at least one lace loop 36 having a base 38 wherein the base contacts at least one reinforcement strip. The number of lace loops is dependent on any number of variables, such as, for example, the size of the brace body. Typically, a brace body has from 1 to 5 lace loops on each medial and lateral side.

As shown in FIG. 4, lace loop 36 is made from a strip of material that is folded back on itself to create a loop which is typically heat welded or ultrasonic welded together. Base 38 of lace loop 36 comprises two layers of the material used in lace loop 36. In an embodiment, the lace loops are made from polyethylene terephthalate fibers, e.g., Dacron. One skilled in the art would understand any durable fabric or plastic could be used for the lace loops.

Figure 5:
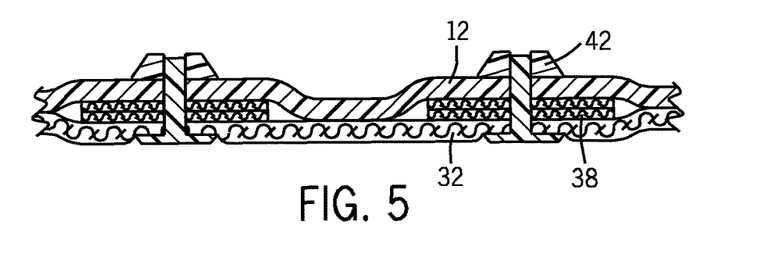
FIG. 5 is a sectional view taken along line 5-5 of FIG. 2.

As shown in FIG. 5, base 38 of lace loop 36 is encapsulated in the polyolefin elastomeric material such that base 38 of lace loop 36 is positioned between an inner most layer of a reinforcement strip and an outer layer of the brace body. The three layers (reinforcement strips, brace body, and lace loops) enhance the strength and durability of the ankle brace.

The three layers are further secured with fasteners 42 that connect all three layers together. Fasteners 42 may be metallic or non-metallic, plastic, fabric or any material of sufficient strength and durability to connect all three layers.

As shown in FIG. 5, fastener 42 secures base 38 of lace loop 36 between the brace body 12 and a reinforcement strip (FIG. 5 depicts second medial reinforcement strip 32). Fasteners 42 bear the sheer load from the closure means. Thus, for example, when the closure means involves laces, the user may apply force in tightening the ankle brace without concern for the durability of the ankle brace.

Referring to FIGS. 1-4, ankle brace 10 may further comprise stabilizing loop 37, which is similar to lace loops 36 except the base of stabilizing loop 37 is not encapsulated in the polyolefin elastomeric material. Instead, stabilizing loop 37 is connected to first medial and lateral reinforcement strips 28, 30 by fastener 42. The base of stabilizing loop 37 is in contact with first medial and lateral reinforcement strips 28, 30 in an area approximately from 1 to 2.5 inches above sole portion 22.

Figure 6:
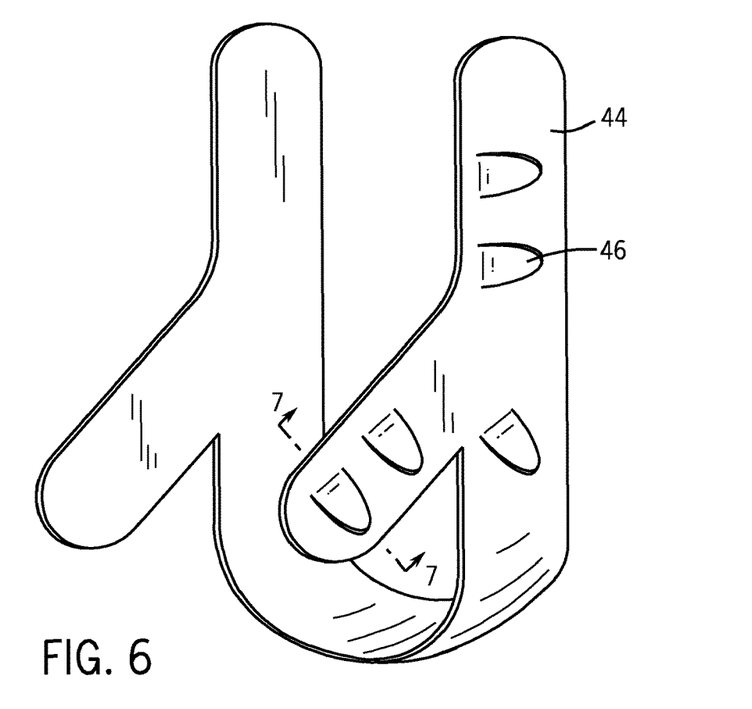
FIG. 6 is a perspective view of an embodiment of a reinforcement strip.

In an embodiment, as shown in FIG. 6, the first reinforcement strips and second reinforcement strips are integrated or otherwise provided as one continuous piece forming unitary reinforcement structure 44. Unitary reinforcement structure 44 may be made of material from the loop pile of a Velcro strip. Unitary reinforcement structure 44 may be made of a stiffer material than that of the brace body. Unitary reinforcement structure 44 may be made of a plastic which may be injection molded. In an embodiment, the width of the reinforcement strips are from 0.5 to 1.5 inches, for example from 0.9 to 1.2 inches. The overall height of unitary reinforcement strip 44 may be from 3 to 12 inches, for example from 8 to 10 inches, for example 9 inches.

Figure 7:
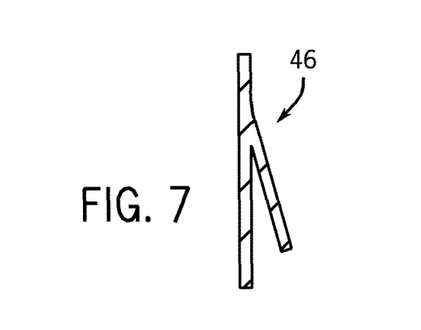
FIG. 7 is a sectional view taken along line 7-7 of FIG. 6.

In an embodiment, unitary reinforcement structure 44 comprises lace hooks 46, a cross section of which is shown in FIG. 7. Lace hooks 46 may be formed of the same plastic material as unitary reinforcement structure 44. Alternatively, lace hooks 46 may be made of a different material than that of unitary reinforcement strip 44. Lace hooks 46 may be of a width from 0.2 to 0.4 inches, for example 0.325 inches. The height of lace hooks 46 may be from 0.1 to 0.2 inches, for example 0.14 inches. Laces may be hooked around lace hooks 46 and tightened to secure ankle brace 10 to the user's ankle. Other closure mechanisms are contemplated in connection with unitary reinforcement structure 44, such as, lace loops and laces.

In an embodiment, an elliptical section above the heel is removed from the back portion of the brace body. The opening is designed to further facilitate dorsiflexion and plantarflexion while maintaining the support necessary for medial-lateral motion and rotation.

An advantage of the ankle brace is that it is specially designed to be durable and re-usable, i.e. usable many times repeatedly.

Method of Manufacture

The present disclosure also provides a method of manufacture of the ankle brace system. In an embodiment, the method includes providing a mold (e.g., plaster, wax, metal, wood, epoxy molds) of a patient's lower extremity. The mold may be created from a 3D image or negative cast of the patient's extremity. Alternatively, instead of a mold being made from a patient's scan or cast, the mold may correspond to a pre-fabricated size. Thus, a patient may choose a pre-fabricated standard size that most closely fits their foot size. The correct size is determined by measuring the instep of a patient by placing a flexible tape around the instep and heel with the ankle at 90 degrees. The measurement and patient's shoe size are used to determine the best pre-fabricated size on a sizing chart.

At least one reinforcement strip is placed on the mold for varus and valgus control. Preferably, first medial reinforcement strip 28 is placed on the mold to extend down medial side portion 14 of brace body 12 and first lateral reinforcement strip 30 is placed on the mold to extend down lateral side portion 20 of brace body 12. In an embodiment, the first medial reinforcement strip and the first lateral reinforcement strip are one continuous reinforcement strip that is placed around heel portion 24 of brace body 12.

Second medial reinforcement strip 32 is placed on the mold such that one end intersects with first medial reinforcement strip 28, and second medial reinforcement strip 32 extends substantially parallel to medial front edge 18 of medial side portion 14 of brace body 12. Second lateral reinforcement strip 34 is placed on the mold such that one end intersects with first lateral reinforcement strip 30, and second lateral reinforcement strip 34 extends substantially parallel to lateral front edge 20 of lateral side portion 16 of brace body 12.

The base of the lace loops are placed on the reinforcement strips. In an embodiment, the base of the lace loops are heat welded or ultrasonic welded together.

Then the polyolefin elastomeric material is formed over the mold, typically by thermoforming or injection molding. During thermoforming the polyolefin elastomeric material is heated to a temperature from 225° F. to 250° F. and placed over the mold, the reinforcement strips and base of the lace loops to produce a brace body. In an embodiment, after the polyolefin elastomeric material is draped over the mold, a vacuum is used to seal the polyolefin elastomeric material over the mold, reinforcement strips and the base of the lace loops. The vacuum may be maintained until the polyolefin elastomeric material returns to room temperature.

The mold is removed once the polyolefin elastomeric material has cooled to room temperature to produce the ankle brace. A cut is made in the polyolefin elastomeric material across the width of the base of a lace loop just anterior of a first reinforcement strip or just dorsal to a second reinforcement strip, from which the lace loop is pulled through to partially expose the lace loop for future lacing. Fasteners are added to further secure the reinforcement strips, base of the lace loops and brace body together. Laces may be added through the lace loops.

In an embodiment, the height of the anterior and dorsal surfaces of the mold are such that the lateral and medial front edges may be overlapped when the ankle brace is tightened by the closing mechanism.

Additionally, in an embodiment, the reinforcement strips and base of the lace loops are laminated in the brace body such that one layer of polyolefin elastomeric material or synthetic fabric (e.g., clarino or lycra) is first placed on the mold, followed by the placement of the reinforcement strips and lace loops. Then an outer layer of polyolefin elastomeric material is placed over the reinforcement strips and lace loops thereby encapsulating the reinforcement strips and lace loops in the brace body. Other closure mechanisms besides lace loops and laces are contemplated and considered within the scope of the invention.

It is specifically intended that the present invention not be limited to the embodiments and illustrations contained herein, but include modified forms of those embodiments including portions of the embodiments and combinations of elements of different embodiments as come within the scope of the following claims.

What is claimed is:

1. An ankle brace arranged to provide varus and valgus control and medial-lateral inversion or eversion control comprising:
a brace body comprising
a medial side portion,
a lateral side portion,
a medial front edge of the medial side portion,
a lateral front edge of the lateral side portion,
a sole portion in a plane at least partially horizontal to the medial and lateral side portions having an arch portion and heel portion, and
a back portion extending from the heel portion to a lower calf portion,
wherein the brace body comprises a polyolefin elastomeric material consisting essentially of a polyolefin selected from the group consisting of an ethylene-butene copolymer and an ethylene-octene copolymer, wherein the polyolefin elastomeric material has a melt index range at 190° C. of less than 0.5 to 30 g/10 min (as measured in accordance with ASTM D 1238), a density of 0.857 to 0.910 g/cm$^3$ (as measured in accordance with ASTM D 792), a melting range of 36° C. to 104° C., a Shore A Hardness of 56 to 96 (as measured in accordance with ASTM D 2240), and a flexural modulus from 3 to 110 MPa (as measured in accordance with ASTM D 790);
a first medial reinforcement strip extending down and along the medial side portion;
a first lateral reinforcement strip extending down and along the lateral side portion;
wherein the first medial reinforcement strip and the first lateral reinforcement strip are one continuous reinforcement strip having a width from 0.5 inches to 1.5 inches and extending below the heel portion of the brace body;
a second medial reinforcement strip having one end intersecting with the first medial reinforcement strip at an angle from 90° to 120°, wherein the second medial reinforcement strip extends substantially parallel to the medial front edge of the medial side portion;
a second lateral reinforcement strip having one end intersecting with the first lateral reinforcement strip at an angle from 90° to 120°, wherein the second lateral reinforcement strip extends substantially parallel to the lateral front edge of the lateral side portion,
wherein the first medial reinforcement strip, the first lateral reinforcement strip, the second medial reinforcement strip, and the second lateral reinforcement strip all contact the brace body; and
at least one closure mechanism having at least a first portion in contact with at least one of the first and second medial reinforcement strips and at least a second portion in contact with at least one of the first and second lateral reinforcement strips, wherein the at least one closure mechanism has an opened position and an engaged position; and
wherein the lateral front edge and the medial front edge overlap when the at least one closure mechanism is in the engaged position.

2. The ankle brace of claim 1 wherein the polyolefin elastomeric material comprises the ethylene-butene copolymer.

3. The ankle brace of claim 1 wherein the first medial reinforcement strip, first lateral reinforcement strip, second medial reinforcement strip and second lateral reinforcement strip are inset into the brace body.

4. The ankle brace of claim 1 wherein the closure mechanism comprises lace loops having a base wherein the base of the lace loop is contacting at least one reinforcement strip.

5. The ankle brace of claim 4 wherein the base of the lace loops, the first medial reinforcement strip, first lateral reinforcement strip, second medial reinforcement strip, second lateral reinforcement strip and brace body are secured together by at least one fastener.

6. The ankle brace of claim 4 wherein the base of the lace loops are between the first medial reinforcement strip, first lateral reinforcement strip, second medial reinforcement strip and second lateral reinforcement strip and brace body.

7. The ankle brace of claim 1 wherein the back portion of the brace body has an elliptical hole to facilitate dorsiflexion and plantarflexion motion.

8. The ankle brace of claim 1 wherein the closure mechanism comprises laces, hooks, loops, hook and loop, elastic, fasteners, or combinations thereof.

9. The ankle brace of claim 1 wherein the lateral front edge and medial front edge of the brace body overlap.

10. The ankle brace of claim 1 wherein the ankle brace is constructed and arranged to be used with a separate essentially standard shoe.

11. The ankle brace of claim 1 wherein the ankle brace is waterproof.

12. A method of manufacturing an ankle brace comprising the steps of:
providing a mold of a lower extremity;
placing at least three reinforcement strips on the mold for varus and valgus control, wherein the at least three reinforcement strips includes (1) a continuous reinforcement strip having a first medial portion, a first lateral portion, and a portion extending below the heel portion of the brace body, wherein the continuous reinforcement strip has a width from 0.5 inches to 1.5 inches, (2) a medial reinforcement strip having one end intersecting with the first medial portion of the continuous reinforcement strip at an angle from 90° to 120°, and (3) a lateral reinforcement strip having one end intersecting with the first lateral portion of the continuous reinforcement strip at an angle from 90° to 120°;
forming a polyolefin elastomeric material over the mold, reinforcement strips and base of lace loops to produce a brace body having a medial side portion, a lateral side portion, a medial front edge of the medial side portion, a lateral front edge of the lateral side portion, a sole portion in a plane at least partially horizontal to the medial and lateral side portions having an arch portion and heel portion, and a back portion extending from the heel portion to a lower calf portion, wherein the medial reinforcement strip extends substantially parallel to the medial front edge and the lateral reinforcement strip extends substantially parallel to the lateral front edge;
wherein the reinforcement strips and base of the lace loops are inset into the polyolefin elastomeric material, wherein the polyolefin elastomeric material consists essentially of a polyolefin selected from the group consisting of an ethylene-butene copolymer and an ethylene-octene copolymer, wherein the polyolefin elastomeric material has a melt index range at 190° C. of less than 0.5 to 30 g/10 min (as measured in accordance with ASTM D 1238), a density of 0.857 to 0.910 g/cm$^3$ (as measured in accordance with ASTM D 792), a melting range of 36° C. to 104° C., a Shore A Hardness of 56 to 96 (as measured in accordance with ASTM D 2240), and a flexural modulus from 3 to 110 MPa (as measured in accordance with ASTM D 790); and removing the mold to produce the ankle brace.

13. The method of claim 12 further comprising the step of placing at least one base of a lace loop on the reinforcement strips before forming the polyolefin elastomeric material over the mold.

14. The method of claim 12 further comprising the step of adding fasteners to further secure the reinforcement strips, the base of the lace loops and the brace body together.

15. The method of claim 12 further comprising thermoforming a polyolefin elastomeric material over the mold before placing at least one reinforcement strip on the mold.

16. The method of claim 12 wherein the lace loops are fed through a cut in the polyolefin elastomeric material along a width of the base of the lace loops just anterior of a first reinforcement strip or just dorsal to a second reinforcement strip.

17. The method of claim 16 further comprising the step of placing laces through the lace loops.

18. The method of claim 12 wherein forming a polyolefin elastomeric material over the mold comprises thermoforming or injection molding of the polyolefin elastomeric material.

* * * * *